United States Patent [19]

Hayhurst et al.

[11] Patent Number: 5,041,129

[45] Date of Patent: Aug. 20, 1991

[54] SLOTTED SUTURE ANCHOR AND METHOD OF ANCHORING A SUTURE

[75] Inventors: John O. Hayhurst, Milwaukie, Oreg.; Alan A. Small, Needham; Jeffrey C. Cerier, Franklin, both of Mass.

[73] Assignee: Acufex Microsurgical, Inc., Mansfield, Mass.

[21] Appl. No.: 548,383

[22] Filed: Jul. 2, 1990

[51] Int. Cl.[5] .............................................. A61B 17/00
[52] U.S. Cl. ..................................... 606/232; 606/139; 606/220; 606/151
[58] Field of Search ............... 606/139, 151, 220, 232, 606/144, 140, 72

[56] References Cited

U.S. PATENT DOCUMENTS

| | | | |
|---|---|---|---|
| 4,235,238 | 11/1980 | Ogiu et al. | 606/145 |
| 4,669,473 | 6/1987 | Richards et al. | 606/220 |
| 4,741,330 | 5/1988 | Hayhurst | 606/86 |
| 4,898,156 | 2/1990 | Gatturna et al. | 606/232 |

Primary Examiner—Stephen C. Pellegrino
Assistant Examiner—Gary Jackson
Attorney, Agent, or Firm—Brooks & Kushman

[57] ABSTRACT

A suture anchor (10) for securing a suture (20) to body tissue (38) in an athroscopic surgical procedure. The suture anchor is an elongatyed tubular member (12) having first and second ends (14,16). The distal or terminal end (24) of the suture is secured to the first or leading end (14) of the suture anchor (10) with the suture (20) extending through the suture anchor (10). A slot (18) is formed on the suture anchor (10) which extends from the second or trailing end (16) of the suture anchor (10) toward the leading end (14) of the suture anchor (10). The suture anchor (10) is inserted in a first position with the suture (20) extending through the suture anchor (10) from the leading end (14) of the suture anchor (10) to the trailing end (16). The suture (20) shifts from the first position approximately 90 degrees to a second position wherein the suture (20) extends from the leading end (14) of the anchor to the base (26) of the slot (18) with the length of the suture anchor (10) extending transverse to the free end (25) of the suture (20) located outside of the suture anchor (10). The method disclosed includes the steps of inserting the suture anchor (10) with the suture (20) extending longitudinally through the anchor (10) and shifting the orientation of the anchor (10) until the suture (20) extends through a slot (18) in the anchor (10) with the anchor (10) disposed in the body tissue (38) generally transverse to the free end (25) of the suture.

16 Claims, 1 Drawing Sheet

U.S. Patent  Aug. 20, 1991  5,041,129
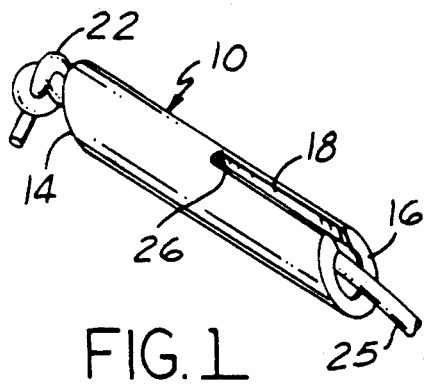
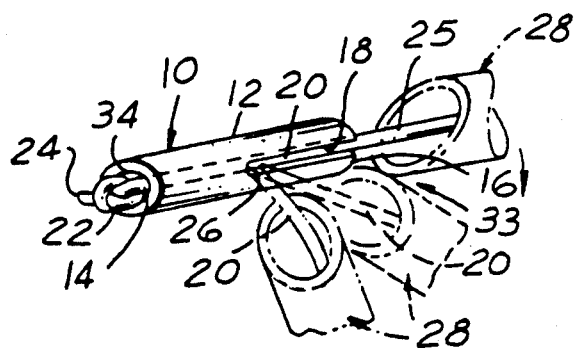
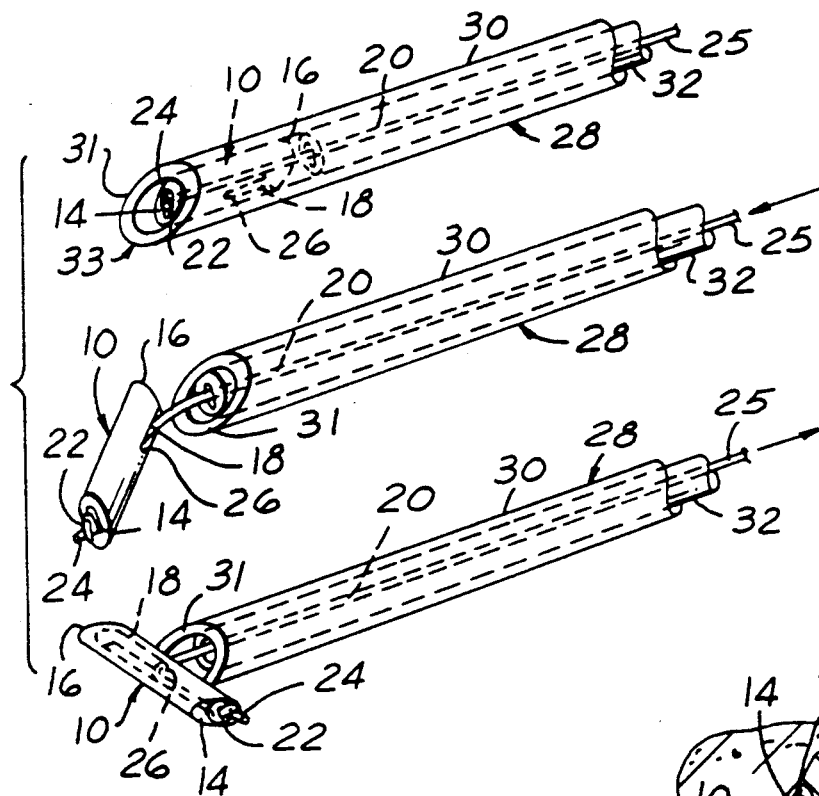
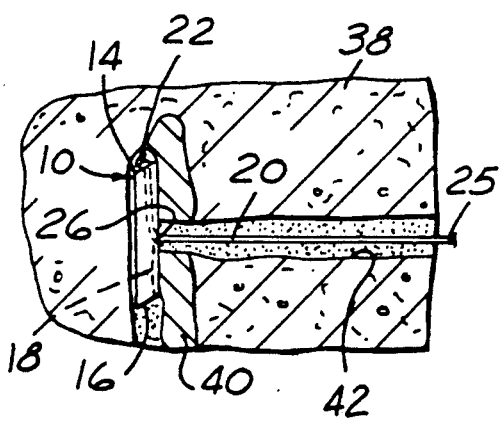
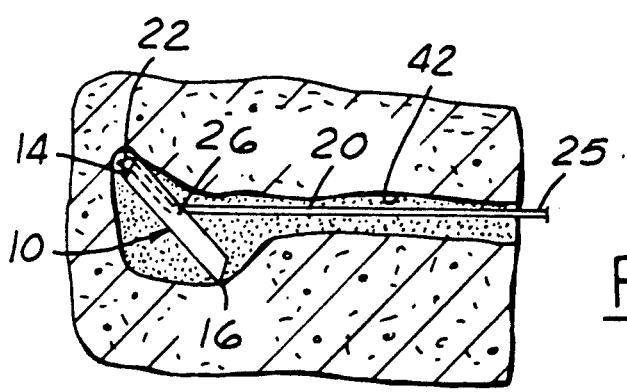

SLOTTED SUTURE ANCHOR AND METHOD OF ANCHORING A SUTURE

TECHNICAL FIELD

The present invention relates to anchors for surgical sutures and more particularly relates to small elongated structures which are attached to a suture and which are inserted lengthwise through a hole in body tissue and deployed by rotating the structure generally transverse to the suture after insertion.

BACKGROUND ART

Suture anchors have been developed for anchoring sutures during arthroscopic surgery with single side access. Such suture anchors are generally inserted with special tools for placement of the suture anchor and manipulation from one side of the body part after insertion.

One example of such a suture anchoring device is disclosed in U.S. Pat. No. 4,669,473 to Richards, et al. which is assigned to the assignee of the present invention. The Richards patent discloses a surgical fastener having a head portion and a filament portion normally arranged in a "T-shaped" configuration. The head portion has at least one pointed end so that when the head portion is implanted in body tissue, the head portion will attach itself securely to the body tissue. The surgical fastener is inserted by a tool including a hollow sheath through which the head of the T-shaped fastener is forced into position by a ram. The filament connected to the head is pulled with the head through a slot in the sheath. The resiliency of the fastener causes it to return to its normal T-shaped configuration with the head disposed generally transverse or at an acute angle to the filament. In this orientation, the pointed ends of the fastener head lodge themselves into the surrounding tissue. The tool is then removed leaving the free end of the filament extending from the tissue for subsequent use by the surgeon.

Another approach to providing a suture anchor intended to be anchored behind cartilage is disclosed in U.S. Pat. No. 4,741,330 to Hayhurst. The Hayhurst suture anchor also has a T-shaped configuration and is deployed for implantation with the ends of the head doubled over and pointing away from the filament. After insertion, the ends of the head due to their natural resiliency tend to return to their normal perpendicular orientation relative to the filament. Alternatively, the T-shaped anchor may be deployed with the filament folded over parallel to the head and forced into position through an elongated tubular insertion tool.

While the above surgical fasteners have proven to be dependable and effective, several disadvantages have been encountered which are addressed by the present invention. For example, the diameter of the opening in the body or tissue required for insertion in each of the above references must be greater than the combined diameter of the head of the T-shaped anchor and the filament. Also, the Richards' anchor is molded in one piece and includes a molded filament which may be more difficult to tie off than a conventional suture. With the Hayhurst anchor, joining the suture material to the plastic anchor sometimes involves intricate manufacturing and quality control procedures.

For arthroscopic procedures, the small space available to operate limits the size of instruments which can be used. Generally if such instruments are made smaller, they are more practical and can be used more efficiently and easily. Similarly, the smaller the hole required for insertion of the surgical instruments, the less trauma is caused to the patient by the operation and the less time it takes for the surgical site to heal.

The suture anchor and suture of the present invention, when installed according to the method of the present invention minimizes these and other problems.

Accordingly, it is a principal object of the present invention to provide an improved single-sided surgical suture fastener which minimizes the diameter of the insertion opening. Another object is to provide an improved surgical suture fastener which is simple and inexpensive to make.

A further object of the present invention is to provide an improved T-shaped suture anchor and a method of constructing it. Still another object is to provide an improved method for deploying a T-shaped surgical suture fastener.

Another object of the present invention is to provide an improved T-shaped suture anchor which has a stronger connection between the suture and the anchor and utilizes the full strength of the suture.

DISCLOSURE OF THE INVENTION

These and other objects of the invention are achieved by a novel suture anchor and suture as described below. A suture anchor and suture in combination are provided comprising a suture and an elongated tubular anchor having a slot extending part way from the trailing end toward the leading end. The suture is knotted or otherwise affixed adjacent its terminal end with the knot engaging the leading end of the anchor. The suture is threaded axially through the anchor from the leading end to the trailing end forming a thin elongated package for insertion. The suture shifts along the slot during deployment to a position wherein the suture extends from an intermediate point on the anchor to form a generally T-shaped surgical suture fastener.

According to another aspect of the present invention, a suture anchor for anchoring a suture to tissue comprises an elongated tube having a leading end and a trailing end. The tube has a slot extending linearly from the trailing end of the tube preferably approximately halfway to the leading end of the tube. The suture is secured to the leading end of the tube. The anchor is rotatable between a first position in which the suture extends completely through the tube and a second position in which the suture extends from the leading end of the tube and exits from the slot.

According to another aspect of the present invention, the ends of the tubular member preferably define leading and trailing ends disposed at oblique angles to the central axis of the tube. The leading end defines a pointed structure which aides in insertion. The oblique angulation of the trailing end assists in rotating the suture anchor to its toggle position forming a T-shaped anchoring structure.

The slot extends linearly from the trailing end of the head and preferably starts at the axial inboard most point of the trailing end (i.e. the point of the trailing end which is closest to the mid-point of the anchor).

The suture anchor and suture may be assembled prior to delivery to the operating room or may be assembled by the surgeon prior to insertion in a patient.

According to the method of making a suture anchor according to the present invention, a T-shaped anchor is formed using a small elongated tubular member having leading and trailing ends. A slot is formed in the tubular member extending from the trailing end to an intermediate point between the two ends. A suture is secured to the leading end of the tubular member and threaded through the tubular member to the trailing end.

The method of deploying the suture anchor comprises the steps of inserting the anchor using a hollow tool with the first end of the anchor being initially inserted by the tool into (or through) the body tissue to a desired depth, generally behind cartilage. As inserted, the suture, which is secured to the first end of the tubular member, extends the length of the anchor. After the anchor is pushed through the end of the tool, tension is applied to the suture causing the anchor to grip the tissue and rotate to a toggle position with the suture being pulled through the slot.

BRIEF DESCRIPTION OF DRAWINGS

FIG. 1 is an elevational view of the suture anchor of the present invention.

FIG. 2 is a perspective view of the suture anchor, suture and a fragmentary view of the installation tool showing the suture anchor as initially inserted, as partially inserted, and as finally in its toggle position.

FIG. 3 is a perspective view of the suture anchor illustrating an enlarged view of the inserting and toggle procedures.

FIG. 4 is a cross-sectional view showing the suture anchor and suture with the anchor inserted behind a section of cartilage.

FIG. 5 is a cross-sectional view showing the suture anchor and suture inserted in soft tissue.

BEST MODE(S) FOR CARRYING OUT THE INVENTION

Referring now to FIG. 1, the anchor 10 of the present invention is shown. The anchor 10 is formed as a tube 12 having a leading end 14 and a trailing end 16 at opposite ends of the tube 12. A slot 18 extends from the trailing end 16 to a point intermediate the leading end 14 and the trailing end 16. The slot 18 preferably extends to the approximate midpoint of the tube 12.

The ends 14 and 16 of the suture anchor are angled as shown. The leading end 14 is angled to allow point 15 to aid in the insertion of the anchor through the body tissue. The trailing edge 16 is angled to aid in rotating the anchor once it is placed in position and to help lead and place the suture into the slot 18. The edge 17 which is the axial outboard most point of the anchor trailing end (i.e. the end of the anchor further from its midpoint) is adapted to grab or dig into the tissue thereby allowing tension on the suture to cause the anchor to toggle or rotate into a T-shaped configuration. The slot 18 is preferably positioned such that it opens at the axial inboard most point 19 of the anchor (i.e. the edge of the slanted end 16 which is closest to the mid-point of the anchor). This allows the slanted end 16 to direct the suture towards and into the slot 18 when the anchor is rotated.

Although it is preferred that the slot 18 extend approximately one-half of the length of the tube 12 (in order to provide substantially equal or equivalent anchoring surfaces on opposite sides of the suture), it is possible within the scope of the present invention for the slot to extend less than or more than such distance, so long as it operates in an equivalent manner and provides sufficient anchoring effects. Of course, extending the slot too far towards the leading end may weaken the tube in an unsatisfactory manner, and not extending the slot a sufficient length may prevent the tube from rotating into a satisfactory anchoring position.

Referring to FIGS. 2 and 3, the anchor 10 is shown with a suture 20 positioned in it. In FIG. 3, the suture 20 as shown in solid lines in an insertion position, and in phantom lines in its partially inserted position and in its deployed or toggle position in solid lines. The suture 20 is attached to the anchor 10 by means of a knot 22. The knot 22 is large enough to prevent slippage of the suture 20 through the tube 12. The knot 22 is formed on the terminal end 24 of the suture 20.

It is understood that other means for securing the suture to the anchor 10 are possible including heat staking, gluing, ultrasonic welding, pinning or other similar means of locking the suture 20 to the anchor 10.

Referring to FIG. 2, insertion of the anchor 10 and suture 20 is illustrated in three phases. Insertion of the anchor is performed a cannulated insertion tool 28 (shown fragmentarily). Upon initial insertion, the anchor 10 and suture 20 are confined within a hollow outer needle 30 of the insertion tool 28. The suture 20 extends from the knot 22 formed at the leading end 14 of the tube 12 through the trailing end 16 of the tube. The suture then extends through the pusher tube 32 which is concentrically located within the outer needle 30. Insertion continues as shown in FIG. 2 to a mid-insertion phase wherein the anchor 10 is pushed beyond the distal end 31 of the outer needle 30 by the pusher tube 32. The anchor 10 then shifts out of alignment with the insertion tool 28 and begins to tip toward a toggle position generally transverse to the axial direction of the suture. The suture is then pulled through the slot toward the base 26 of the slot by applying tension to the suture 20.

As stated above, preferably the leading end 14 of the tube 12 defines a leading face 34 which is obliquely angled relative to the central axis of the tube 12. A trailing face 36 is preferably formed on the trailing end 16 of the tube 12 and preferably lies in a plane parallel to that of the leading face 34 and also obliquely angled relative to the central axis of the tube 12. The trailing face 36 functions to aide in tipping the anchor 10 toward its toggle position after it is free from the outer needle of the insertion tool 28.

The angular orientation of the leading faces creates relatively sharp edges which facilitates locking the anchor 10 in soft tissue. Alternatively, the leading and trailing faces 34 and 36 could be substantially perpendicular to the axis of the tube 12. In the final insertion step (illustrated in FIGS. 2 and 3), the anchor 10 is in a toggle position relative to the length of the suture 20 with the suture 20 exiting the tube 12 at the base 26 of the slot 18.

The leading face of the outer needle 30 of the insertion tool 28 is preferably slanted as shown in FIGS. 2 and 3. Also the leading edge 33 of the face has a sharpened tip. This structure allows the needle 30 to penetrate the skin and/or be moved into position more easily for installation of the anchor. Also, in order to prevent "coring" of tissue or skin when the tool 28 is utilized, preferably the anchor 10 is positioned in the needle 30 substantially flush with the distal end or leading face during insertion. For this purpose, if desired, the angle of the leading face of the outer needle 30 can be the same as the angle of the leading face 34 of the anchor tube 12.

As an alternate embodiment of the insertion tool 28, a thin solid pusher rod (not shown) can be utilized in place of the hollow pusher tube 32 shown in FIG. 2. Once the anchor and suture 20 are positioned in the hollow outer tube 30, the pusher rod can be inserted in the tube and used to push the anchor into its installation and anchoring positions. The use of a pusher rod eliminates the step of threading the suture through the pusher tube. With the exception of use of a pusher rod for a pusher tube, the remainder of the suture anchor installation procedure is the same.

Referring now to FIG. 4, a preferred use of the anchor 10 of the present invention is shown wherein the anchor is inserted in body tissue 38 and anchored to cartilage 40. Holes 42 and 44 are formed in the body tissue 38 and cartilage 40, respectively, by use of any conventional surgical drilling or hole forming means. When the anchor 10 of the present invention is used to secure a suture to cartilage, the insertion tool is inserted through the holes 42 and 44 until the end 31 passes through the cartilage 40. The anchor 10 is then pushed out of the insertion tool and rotated to its toggle position as previously described relative to FIGS. 2 and 3.

Referring now to FIG. 5, use of the anchor 10 of the present invention is shown in soft body tissue 38. A hole 42 is formed in the soft tissue either by the insertion tool or by a prior incision. The anchor 10 and suture 20 are inserted into the hole 42 through use of the insertion tool and the anchor is shifted by applying tension on the suture 20 after the anchor 10 is free from the distal end 31 of the outer needle 30. The leading and trailing ends 14 and 16 of the anchor 10 shift from an insertion position wherein the leading end is first inserted into the tissue to a position wherein the leading and trailing ends assume an approximately perpendicular or toggle position relative to the length of the suture 20.

As indicated, preferably the suture anchor is used to affix a suture to body tissue, generally behind cartilage although it can also be used to affix a suture in body tissue alone. In addition, the suture anchor can be passed entirely through body tissue or cartilage and be positioned on the opposite side outside the body or where body tissue is not present. The installation and operation of the invention will be the same.

The anchor 10 may be made of either a bioabsorbable material or a non-absorbable permanent material. Preferred absorbable materials include polyglycolic acid, polylactic acid or trimethylene carbonate copolymers. Preferred non-absorbable materials include acetal homopolymers or copolymers, polyethylene, polypropylene, polyester and copolymers thereof. The suture material may be any conventional type of suture material, such as Ticron, or Dexon brand sutures which are trademarks of Davis & Geck.

With the present invention, there is not a problem securely affixing the suture to the anchor. The suture does not have to be molded into the anchor which sometimes creates strength problems, but instead utilizes a mechanical fastening system which insures a strong and secure affixation. Also, the bending of the suture at the end of the slot when the anchor is installed in place keeps the full strength of the suture at that point. Fasteners which have a molded head and filament portion often have strength problems caused by the head being bent parallel to the filament during insertion.

The above-described preferred embodiments are intended to be illustrative of the invention which may be modified within the scope of the appended claims.

I claim:

1. An anchor for securing a strand of suture material in the body comprising a tube having a leading end and a trailing end, a slot extending from said trailing end to a point intermediate said leading and trailing ends said trailing end defining a trailing face disposed at an oblique angle to the central axis of the tube.

2. The anchor of claim 1 wherein said leading end defines a leading face disposed at an oblique angle to the central axis of the tube.

3. The anchor of claim 1 wherein the slot extends linearly to a slot base.

4. The anchor of claim 1 wherein the slot extends from the axially inboard region of the trailing face to a slot base.

5. An anchor and a strand of suture material in combination, said anchor comprising a tube having a leading end and a trailing end, a slot extending from said trailing end toward said leading end, and means for attaching said strand of suture material to the leading end of the tube with the strand extending from the leading end at least partially through the tube.

6. The suture anchor and strand of suture material of claim 6 wherein said means for interlocking is a knot tied in the strand at a terminal end of the strand which engages the leading end of the tube when tension is applied to the other end of the strand.

7. The suture anchor and strand of suture material of claim 5 wherein said strand of suture material is shiftable between an insertion position in which the strand exits said tube at the trailing end and a toggle position in which said strand exits the tube through said slot.

8. A suture anchor and suture in combination comprising:
   a suture,
   an elongated tubular anchor,
   said suture having a knot tied adjacent a terminal end of the suture and engaging a first end of the anchor,
   said anchor having a slot extending from a second end to a slot base intermediate the first and second ends, and
   said suture being threaded through the anchor from the first end axially through the anchor and through the second end in an insertion position and being shifted through the slot during deployment to a deployed position wherein the suture extends from the anchor at the slot base.

9. The anchor of claim 8 wherein said second end defines a trailing face disposed at an oblique angle to the central axis of the tube.

10. The anchor of claim 9 wherein the slot extends from the axially inboard region of the trailing face.

11. The anchor of claim 8 wherein said first end defines a leading face disposed at an oblique angle to the central axis of the tube.

12. The anchor of claim 8 wherein the slot extends linearly along the tube.

13. A suture anchor for anchoring a suture to cartilage comprising:
   an elongated tube having first and second ends,
   means for securing the suture to the tube at said first end of the tube with the suture being partially threaded through the tube;

said tube having a slot linearly extending from said second end to a midpoint located intermediate the first and second ends of the tube;

said anchor being shiftable between a first position in which the suture extends completely through said tube and a second position in which the suture extends from the first end of said tube through said tube to the midpoint of the tube and exits said tube at the midpoint.

14. A method of anchoring a suture in the body with a T-bar anchor, said T-bar anchor being an elongated tubular member having first and second ends, said suture being secured to said first end, second end having a slot extending to the approximate midpoint of the tubular member with said suture being threaded through the tubular member, said method comprising the following steps:

inserting a hollow tool having an outer needle and a pusher means, the T-bar anchor being initially disposed in the outer needle with the first end being initially inserted into body tissue to a desired depth, the suture extending from the first end of the tubular member through the second end and being routed through the pusher tube;

pushing the anchor with said pusher means through the end of the tool with a shiftable element in the hollow tool;

applying tension to the suture to cause the suture to shift the tubular member to a toggle position with the suture shifting through the slot from the second end toward the approximate midpoint wherein the suture exits the tubular member at the approximate midpoint; and removing said tool from the tissue.

15. The method of claim 14 wherein said second end of said tubular member is an obliquely angled trailing face which assists in shifting the tubular member to the toggle position.

16. The method of claim 14 wherein said pusher means comprises a hollow tube and said suture is threaded therethrough.

* * * * *